(12) United States Patent
Bonnette et al.

(10) Patent No.: US 7,219,799 B2
(45) Date of Patent: May 22, 2007

(54) PACKAGING SYSTEM WITH OXYGEN SENSOR

(75) Inventors: Michael J. Bonnette, Minneapolis, MN (US); Eric J. Thor, Arden Hills, MN (US)

(73) Assignee: Possis Medical, Inc., Minneapolis, MN (US)

( * ) Notice: Subject to any disclaimer, the term of this patent is extended or adjusted under 35 U.S.C. 154(b) by 6 days.

(21) Appl. No.: 10/748,452

(22) Filed: Dec. 30, 2003

(65) Prior Publication Data

US 2004/0188304 A1 Sep. 30, 2004

Related U.S. Application Data

(60) Provisional application No. 60/437,624, filed on Dec. 31, 2002.

(51) Int. Cl.
*B65D 85/20* (2006.01)
(52) U.S. Cl. .................... 206/459.1; 206/807
(58) Field of Classification Search ................ 206/807, 206/459.1, 204–213.1, 438, 484, 484.2; 436/1, 436/3, 135; 426/136
See application file for complete search history.

(56) References Cited

U.S. PATENT DOCUMENTS

| | | | | |
|---|---|---|---|---|
| 4,166,807 A | * | 9/1979 | Komatsu et al. | 502/62 |
| 5,014,494 A | * | 5/1991 | George | 53/425 |
| 5,196,245 A | * | 3/1993 | DeRudder et al. | 428/35.5 |
| 5,399,658 A | * | 3/1995 | Archey et al. | 528/198 |
| 5,474,194 A | * | 12/1995 | Heilman et al. | 215/230 |
| 5,583,047 A | * | 12/1996 | Blinka et al. | 436/5 |
| 5,881,534 A | * | 3/1999 | Ahlqvist et al. | 53/403 |
| 6,161,695 A | * | 12/2000 | Nicolais | 206/438 |
| 6,166,116 A | * | 12/2000 | Sleeckx | 524/168 |
| 6,485,657 B1 | * | 11/2002 | Funakoshi et al. | 252/478 |
| 6,494,314 B1 | * | 12/2002 | Lamborne et al. | 206/0.6 |
| 6,927,063 B2 | * | 8/2005 | Moreton et al. | 436/39 |
| 2004/0050740 A1 | * | 3/2004 | Lewis | 206/459.1 |

OTHER PUBLICATIONS

Medical Device & Diagnostic Industry, Aug. 1997, Article by Nancy J. Hermanson et al.*
Material Data Sheet for Dow Calibre 2081 polycarbonate revealing the color stability for which the material was created.*

* cited by examiner

*Primary Examiner*—Mickey Yu
*Assistant Examiner*—Jerrold Johnson
(74) *Attorney, Agent, or Firm*—Hugh D. Jaeger, Esq.

(57) ABSTRACT

A packaging system or storage arrangement that includes provision to indicate the presence of oxygen. An oxygen-sensitive material is placed inside a sealable container. Air is evacuated from the sealable container and the sealable container is sealed to isolate the oxygen-sensitive material from oxygen. The sealable container is then irradiated with an effective amount of radiation to activate the oxygen-sensitive material such that the oxygen-sensitive material will undergo a visual change in the presence of oxygen after the oxygen-sensitive material has been irradiated. The visual change provides an indication of the presence of oxygen inside the sealable container.

15 Claims, 5 Drawing Sheets

T = 1 WEEK

T = 0

PACKAGING SYSTEM WITH OXYGEN SENSOR

CROSS REFERENCES TO RELATED APPLICATIONS

This application claims the benefit of U.S. Provisional Application No. 60/437,624, filed Dec. 31, 2002, incorporated herein in its entirety by reference. This application is also related to U.S. patent application Ser. No. 10/007,788 filed Nov. 6, 2001, entitled "Gas Inflation/Evacuation System and Sealing System for Guidewire Assembly Having Occlusive Device", incorporated herein in its entirety by reference, now U.S. Pat. No. 6,942,678 issued Sep. 13, 2005.

FIELD OF THE INVENTION

The present invention relates to the field of packaging of sterile or oxygen-sensitive products, such as medical products and food products. More particularly, the present invention is directed to methods and arrangements for packaging oxygen-sensitive items whereby a change in appearance of a material visually indicates the presence of oxygen inside the packaging.

BACKGROUND OF THE INVENTION

In certain applications, such as pharmaceutical storage or food processing, it is desirable to package the product in a controlled atmosphere or environment to ensure freshness, to promote proper chemical activity, or to prevent microbial contamination. The controlled atmosphere can be an inert gas such as nitrogen or carbon dioxide, or it could be a noble gas. In some applications, the controlled environment could be a vacuum. In those applications where a controlled atmosphere or environment is desirable, it may be beneficial to be able to determine that the desired controlled atmosphere or environment has not been compromised. The presence of oxygen in a previously evacuated sample indicates that atmospheric penetration has occurred and that the controlled atmosphere has been compromised. Thus, oxygen detection is one method for determining if a controlled atmosphere has been breached.

In the medical and food processing industries, it may be desirable to sterilize medical and food products after these products have been placed inside containers with controlled environments. The medical and food processing industries have sterilized some appropriate products with gamma radiation. Gamma radiation, which can be derived from cobalt 60, is lethal to bacteria and other microorganisms due to the effect that the radiation has on living cells. In addition, gamma radiation can be detrimental to some chemical systems and compositions. The dose or amount of radiation absorbed is typically measured in either Megarads or Kilograys, where 1 Megarad is equivalent to 10 Kilograys. In general, a 2.5 Megarad, or 25 Kilogray, dose of gamma radiation can be sufficient to kill most microorganisms.

Gamma radiation is composed of high energy photons with wavelengths generally shorter than about 0.1 nm. Gamma radiation is emitted from atomic nuclei during radioactive decay and generally follows the ejection of beta rays from the nucleus. X-rays are similar to gamma rays in the sense that both are highly energetic and penetrating forms of radiation. However, gamma rays usually have shorter wavelengths than X-rays, and as a result, gamma rays are slightly higher in energy than X-rays.

As a result of the increased use of gamma radiation sterilization and packaging in controlled environments, there is a need for oxygen-sensitive materials that can be placed inside medical and food product containers which can detect the presence of oxygen after the container has been irradiated, and possibly sterilized, with gamma radiation.

Currently, there are several types of oxygen, and oxidation, sensors designed to be used in packaging applications. See, for example, U.S. Pat. No. 4,526,752 to Perlman et al., U.S. Pat. No. 5,096,813 to Krumhar et al., U.S. Pat. No. 6,399,387 to Stenhom et al., and U.S. Pat. No. 6,325,974 to Ahvenainen et al. However, none of these patents is directed toward oxygen-sensitive materials that are activated by radiation. Furthermore, the above-mentioned sensors are not suitable to form component parts for other devices. With the volume of medical devices and food products being produced, it would be desirable to provide an oxygen sensor that was easily stored in oxygen-rich environments and could be activated upon exposure to gamma radiation in the absence of oxygen.

SUMMARY OF THE INVENTION

In some embodiments, the present invention is directed toward a method and packaging system or storage arrangement including a container and an oxygen-sensitive material that is suitable for detecting the presence of oxygen inside the container after the container has been irradiated with radiation. In addition, at least some of the oxygen-sensitive materials of the present invention can be incorporated into component parts for some other devices, such as medical devices. By using the oxygen-sensitive material as a component piece of a medical device, or other device, the device itself becomes an oxygen indicator, thereby removing any ambiguity regarding the contact of the device with the ambient atmosphere. Furthermore, some of the oxygen-sensitive materials of the present invention can be stored in oxygen-rich environments because they do not become "active" until the oxygen-sensor material has been exposed to radiation. In some embodiments, the oxygen-sensitive materials are activated in an oxygen-free environment. As used in this application, the term "activated" or "active" means that the oxygen-sensitive material will undergo a visual change when exposed to oxygen. Thus, the present invention creates an effective storage arrangement having means for detecting the presence of oxygen, and ultimately for determining a failure in packaging, in applications involving radiation sterilization.

In one embodiment of the present invention, a sealable container adapted to isolate the contents thereof from the ambient atmosphere is provided with an oxygen-sensitive material located within the sealable container. The oxygen-sensitive material can be any material that undergoes a visual change when in contact with oxygen after the oxygen-sensitive material has been irradiated with gamma radiation in an oxygen-free environment.

In another embodiment of the present invention, a medical device is provided that contains a structural element which is composed of an oxygen-sensitive polymeric material. The oxygen-sensitive polymeric material will visually indicate if the medical device has been exposed to oxygen. Thus, in this embodiment of the present invention, the product, i.e., the medical device and the oxygen-sensitive material, is a single unit. In a further embodiment of the present invention, a medical device comprising a polycarbonate material is provided. The polycarbonate material used in this embodiment of the present invention will visually indicate the presence of oxygen after being irradiated with gamma radiation if oxygen is present.

In a method according to the present invention, an oxygen-sensitive storage arrangement is produced by placing an oxygen-sensitive material inside a sealable container. The oxygen-sensitive material can be any material that undergoes a visual change with oxygen after the oxygen-sensitive material has been irradiated with radiation. The atmospheric contents of the sealable container are then removed and the sealable container is sealed to isolate the oxygen-sensitive material inside the sealable container. The sealable container is then irradiated with an effective amount of radiation so that the oxygen-sensitive material will undergo a visual change if the oxygen-sensitive material contacts oxygen.

BRIEF DESCRIPTION OF THE DRAWINGS

Other objects of the present invention and many of the attendant advantages of the present invention will be readily appreciated as the same becomes better understood by reference to the following detailed description when considered in connection with the accompanying drawings, in which like reference numerals designate like parts throughout the figures thereof and wherein:

FIGS. 6, 6a and 6b are top views of two distal occlusion inflation devices each containing a component piece comprising an oxygen-sensitive material, with the device of FIG. 6b having just been exposed to air and with the device of FIG. 6a having been exposed to air for one week and thereby illustrating the color change associated with an oxygen-sensitive material of the present invention; and, FIGS. 7, 7a and 7b are top views of two crimper devices that show a visual change associated with one embodiment of the present invention, with the device of FIG. 7b having just been exposed to air and with the device of FIG. 7a having been exposed to air for one week.

DETAILED DESCRIPTION OF THE PREFERRED EMBODIMENTS

In one embodiment of the present invention, a packaging system or storage arrangement is provided that comprises a sealable container adapted to isolate the contents of the sealable container from the ambient atmosphere. In this embodiment, an oxygen-sensitive material is located inside the sealable container. The oxygen-sensitive material can undergo a visual change upon contact with oxygen after the oxygen-sensitive material has been irradiated with radiation in the absence of oxygen. In one embodiment, the visual change is a color change. In some embodiments, the sealable container can isolate a medical product from the ambient atmosphere, while in other embodiments the sealable container can isolate a food product. In one embodiment, the sealable container isolates a distal occlusion inflation device from the ambient atmosphere. In some embodiments, the oxygen-sensitive material comprises a polycarbonate material. In one embodiment, the polycarbonate material comprises Dow Calibre™ 2081 polycarbonate material. In some embodiments, the sealable container is resealable, while in other embodiments the sealable container is not resealable. In some embodiments, the sealable container is substantially free of oxygen. In one embodiment, the sealable container is a foil pouch.

In another embodiment of the present invention, a medical device comprising a structural element is provided. The structural element comprises an oxygen-sensitive polymeric material that can visually indicate if the medical device has been exposed to oxygen. In one embodiment, the medical device is a distal occlusion inflation device. In some embodiments, the oxygen-sensitive polymeric material can visually indicate the presence of oxygen after the oxygen-sensitive polymeric material has been irradiated by an effective amount of radiation. In one embodiment, the oxygen-sensitive polymeric material comprises Dow Calibre™ 2081. In some embodiments, the radiation is gamma radiation, while in other embodiments the radiation is X-ray radiation. When the oxygen-sensitive polymeric material comprises Dow Calibre™ 2081, an effective amount of gamma radiation is from about 25 Kilograys to about 45 Kilograys. In some embodiments, the structural element is attached to a background material which enhances visibility of the visual indication of the presence of oxygen.

In another embodiment, a storage arrangement comprising a sealable container and an oxygen-sensitive material is provided. In this embodiment, the oxygen sensitive material will not function as an oxygen detector until the oxygen-sensitive material has been activated. In some embodiments, the oxygen-sensitive material can be activated by irradiating the oxygen-sensitive material with radiation in an oxygen-free environment. In one embodiment, the oxygen-sensitive material is activated by irradiating the material with gamma radiation.

Figure 1:
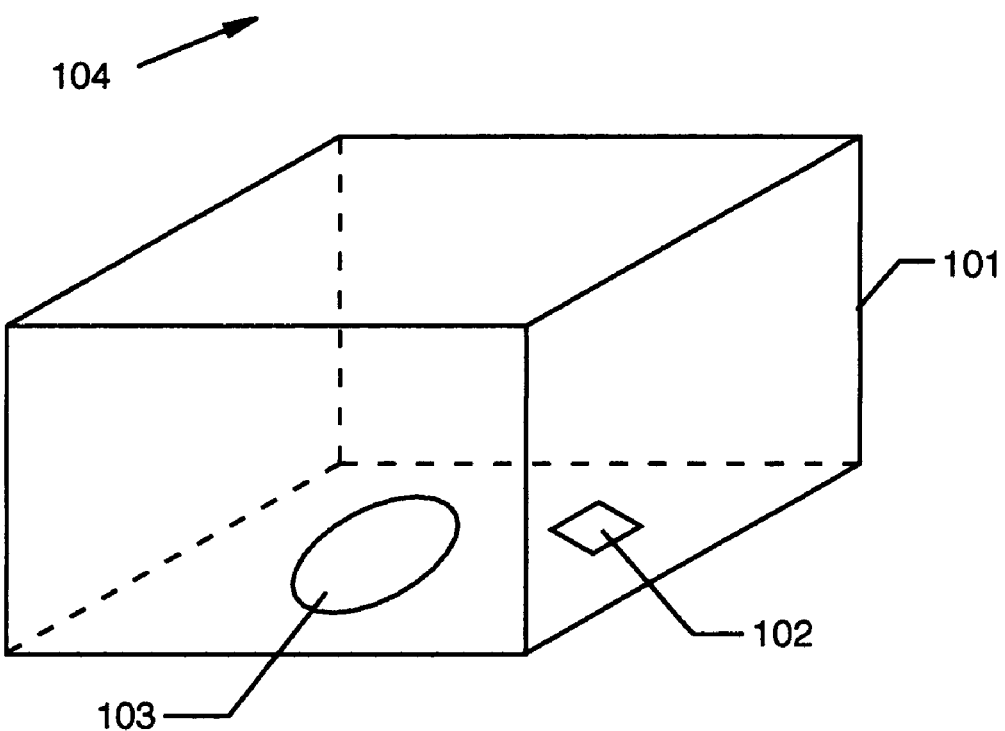
FIG. 1 is a schematic perspective view of one embodiment of a storage arrangement according to the present invention where a container and an oxygen-sensitive material are provided and where structures within the container have been made visible while hidden edges of the container are shown with phantom lines.

FIG. 1 shows schematically one embodiment of a packaging system or storage arrangement according to the present invention. As shown in FIG. 1, a sealable container 101 (depicted representatively) isolates a product 103 (also depicted representatively) from the ambient atmosphere 104. An oxygen-sensitive material 102 (illustrated representatively) is located inside the sealable container. The oxygen-sensitive material 102 can visually indicate the presence of oxygen inside the sealable container 101. In one embodiment, the visual indication of the presence of oxygen will be a change in color of the oxygen-sensitive material 102. The oxygen-sensitive material 102 of the present invention can be any material that will visually indicate the presence of oxygen after the oxygen-sensitive material 102 has been irradiated by radiation. A suitable choice for the oxygen-sensitive material 102 is a polycarbonate resin manufactured by Dow Chemical Company and sold under the trademark Dow Calibre™ 2081. In one embodiment, when the oxygen-sensitive material 102 comprises Dow Calibre™ 2081, the oxygen-sensitive material 102 will visually indicate the presence of oxygen after being irradiated with gamma radiation. A suitable amount of gamma radiation has been found to be from about 25 Kilograys to about 45 Kilograys. In other embodiments, the radiation used can be X-ray radiation.

Figure 2:
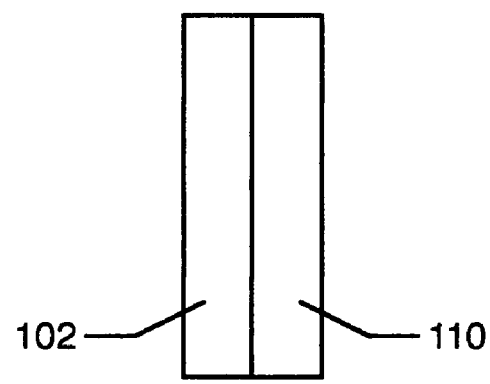
FIG. 2 is a side view of an oxygen-sensitive material attached to a background material that enhances the visual change of the oxygen-sensitive material.

The oxygen-sensitive material 102 as shown representatively in FIG. 1 can be formed into any desirable shape for use in the present invention. In one embodiment, the shape of the oxygen-sensitive material is a rectangular chip. As shown in FIG. 2, the oxygen-sensitive material 102 optionally can be attached to a background material 110 to enhance the visibility of the visual change of the oxygen-sensitive material 102. The background material can be composed of metal, plastic, paper, or any other suitable material that will enhance the visibility of the visual change. For example, a blue background material would make a yellow indicator appear green. Potential background materials could also have the word "exposed" written across the background material in a color such that upon contact with oxygen, the word "exposed" would become visible. As another option, the oxygen-sensitive material can be arranged to form at least one symbol that assists in interpreting the visual change of the oxygen-sensitive material. In embodiments that employ a background material 110, the background material 110 can be attached to the oxygen-sensitive material 102 through the use of generally known adhesives or mechanical fasteners.

The sealable container of the present invention as shown representatively at 101 in FIG. 1 can be composed of any substance that will transmit radiation and that is impermeable to gas, especially oxygen. Examples of suitable materials for the container are metals, glass, gas-impermeable plastics, gas-impermeable thermosets and rubbers, and gas-impermeable foil pouches. In one embodiment, the sealable container is a foil pouch of multi-layer construction comprising a silicone oxide treated PET layer, a foil layer, a biaxially oriented nylon layer, and a polyethylene layer. The gas-impermeable plastic containers of the present invention can be either rigid or flexible. Suitable plastic materials for the gas-impermeable plastic containers include, but are not limited to, gas-impermeable polyethylenes, polystyrenes, polycarbonates, nylons and polyethylene terephthalates. Potential thermoset and rubber materials for the sealable containers include gas-impermeable phenol formaldehydes, urea formaldehydes, natural rubbers and nitrile rubbers.

Figure 3:
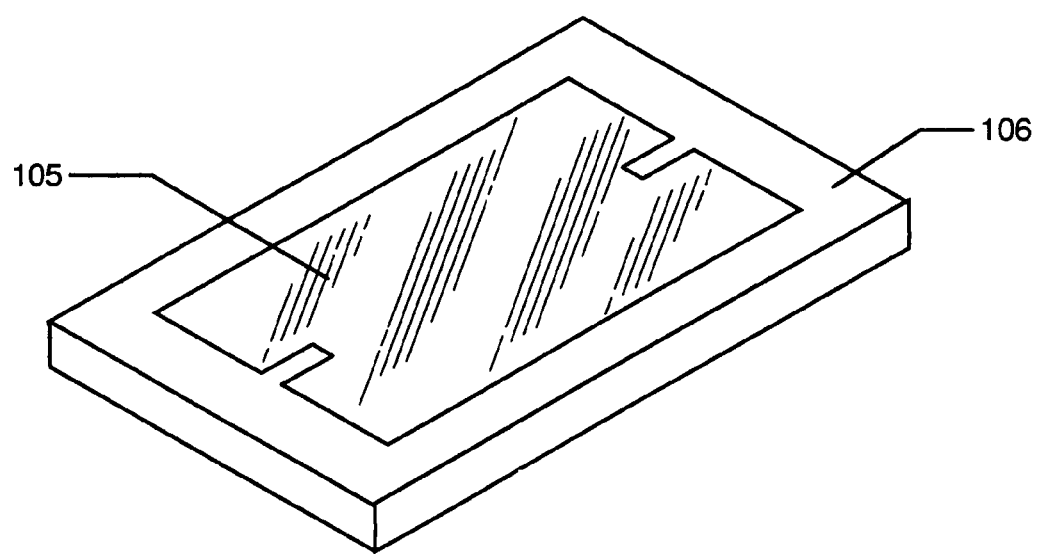
FIG. 3 is a perspective view of one embodiment of a storage container of the present invention.
Figure 4:
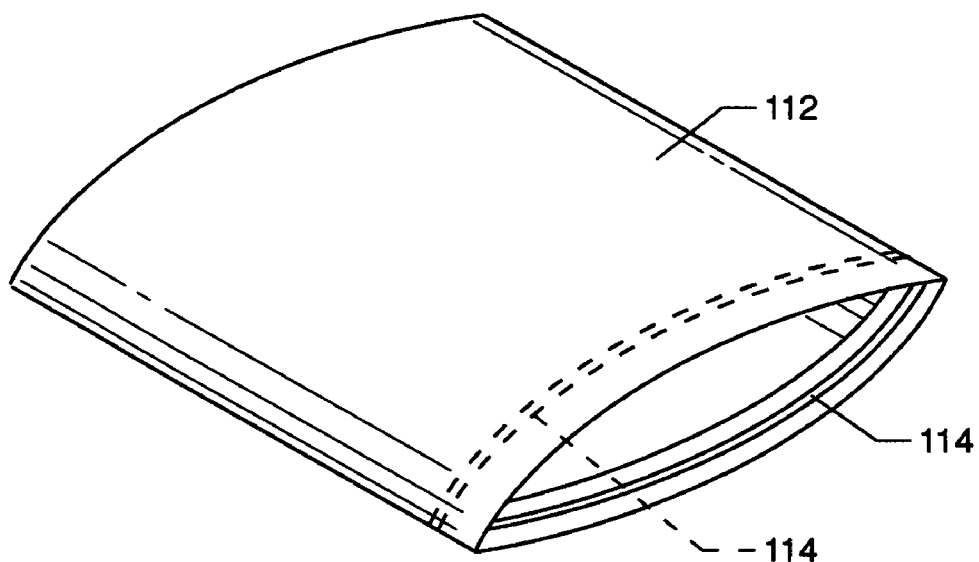
FIG. 4 is a view of a resealable container that can be used in the present invention.
Figure 5:
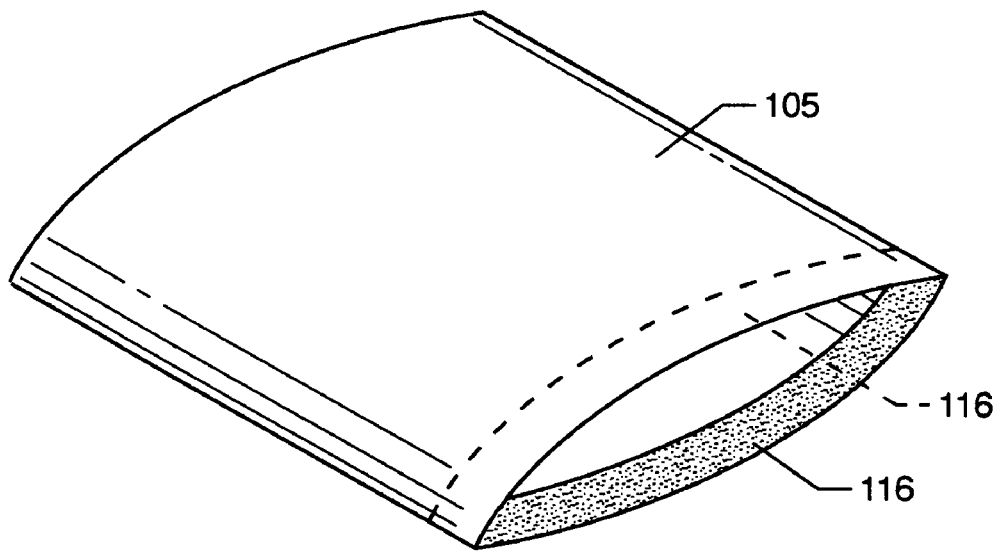
FIG. 5 is a view of a foil pouch showing a plastic coating that can be heated to seal the foil pouch.

The sealable container 101 shown representatively in FIG. 1 can be sealed by any conventional means known to be used in the packaging industries including thermal seals, adhesive seals, or airtight mechanical closures such as caps or lids; and the sealable container can be a container that is resealable or a container that is not resealable. As shown in FIG. 3, one specific embodiment of the sealable container 101 shown in FIG. 1 is a gas-impermeable foil pouch 105 with a protective cardboard packaging 106. FIG. 4 shows another example comprising a resealable pouch 112 with closure means 114 on at least one end of the resealable pouch 112 that permits the resealable pouch 112 to be optionally resealed. When the sealable container is a gas-impermeable foil pouch 105, a heat sealer can be used to heat plastic coatings located on the inside top and bottom of the foil pouch. FIG. 5 shows one embodiment of foil pouch 105 with plastic coatings 116 located on the inside top and bottom of the foil pouch 105. Heating will cause the plastic coatings on the top and bottom to flow together and seal the foil pouch 105.

The product 103 contained within the sealable container 101 can be any product in which a controlled oxygen-free environment is desirable or necessary. Suitable products for the present invention include, but are not limited to, medical devices, pharmaceuticals, and food products.

In one embodiment, a storage arrangement is provided that comprises a sealable container 101 and an oxygen-sensitive material. In this embodiment, the oxygen-sensitive material will not function as an oxygen indicator until the oxygen-sensitive material has been activated. One method of activating the oxygen-sensitive material is by irradiating the material. In some embodiments, suitable forms of radiation for activating the oxygen-sensitive material include gamma radiation and X-ray radiation. In one embodiment, the oxygen-sensitive material comprises Dow Calibre™ 2081 polycarbonate resin. When the oxygen-sensitive material comprises Dow Calibre™ 2081, a dose of gamma radiation from about 25 Kilograys to about 45 Kilograys will activate the material. While not wanting to be limited to a particular theory, it is believed that the oxygen-sensitive property of the Dow Calibre™ 2081 material is likely due to the dye used to color the material or the stabilizers used to protect the material from degradation.

Figure 6A:
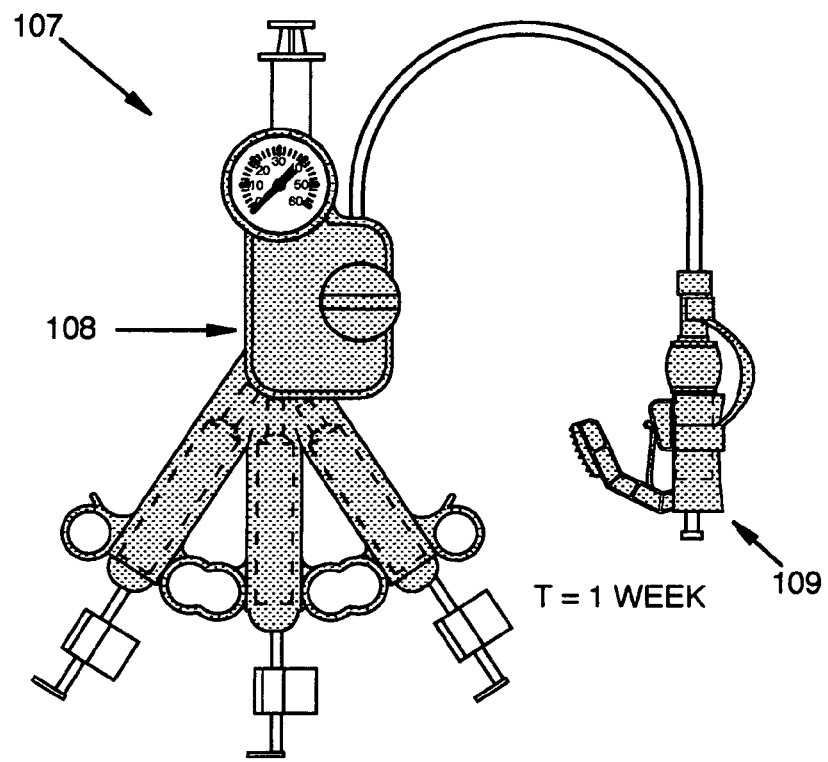
Figure 6B:
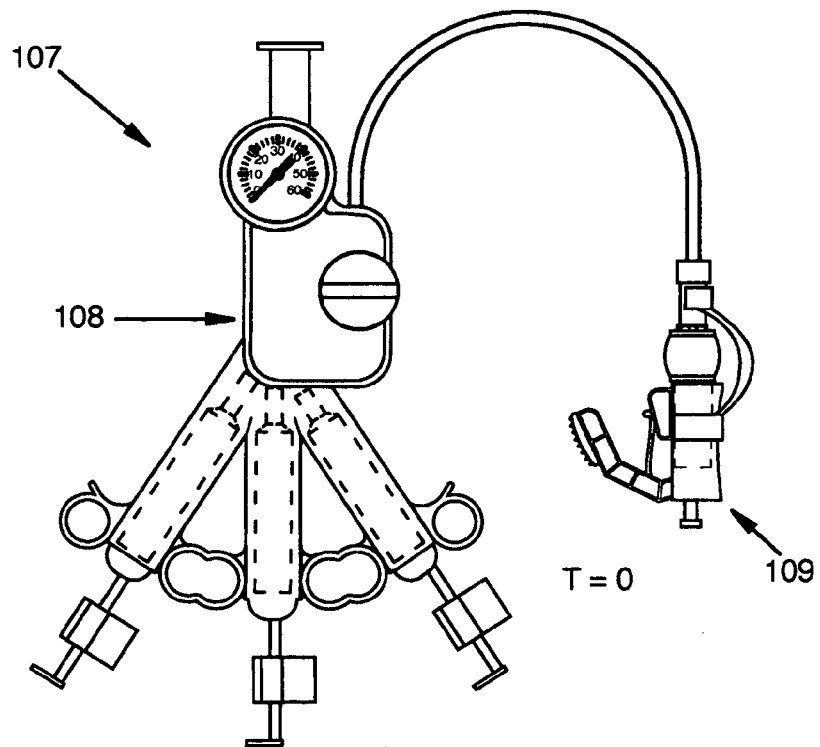

In another embodiment of the present invention, a medical device within a container contains a component piece that is composed of an oxygen-sensitive polymeric material. FIGS. 6a and 6b show one possible embodiment where a medical device 107 has a component piece that is composed of an oxygen-sensitive polymeric material. The medical device 107 is a distal occlusion inflation device available under the trademark GuardDOG which uses $CO_2$ as the inflation medium and which generally comprises a main body 108 and a crimper device 109. In this embodiment, both the crimper device 109 and the main body 108 are composed of an oxygen-sensitive polymeric material. One reason for using an oxygen-sensitive polymeric material in this application is because the inflation medium needs to be relatively free from oxygen in order to prevent the release of oxygen or ambient air into the blood stream in the event that the distal occlusion inflation device would burst, thereby causing a potential embolism. By using $CO_2$ as the inflation medium, the inflation gas can be easily absorbed into the blood stream in the event that the inflation device fails. The oxygen-sensitive polymeric material permits the operator to confirm that the gas within the device that will be used to inflate the inflation device does not include any significant amount of oxygen prior to the use of the device.

In one embodiment, the oxygen-sensitive polymeric material is composed of Dow Calibre™ 2081 polycarbonate resin. When a medical device with an oxygen-sensitive polymeric component piece comprising Dow Calibre™ 2081 is irradiated with gamma radiation, in the absence of oxygen, the oxygen-sensitive material becomes activated and will undergo a visual change if oxygen contacts the material. In one embodiment, the visual change, or indication, is a color change. It has been found that from about 25 Kilograys to about 45 Kilograys of gamma radiation will activate Dow Calibre™ 2081.

An example of the visual change, which indicates the presence of oxygen, associated with this embodiment of the present invention can be seen in FIGS. 6a and 6b by comparing the color of the main body 108 and the crimper device 109 of the medical device 107 shown in FIG. 6a with the color of the main body 108 and the crimper device 109 of the medical device 107 shown in FIG. 6b, the stippling in FIG. 6a representing a change in color from the showing in FIG. 6b. The elapsed time, after exposure to oxygen, before a visible change can be detected is generally 1–8 hours, preferably 1–2 hours. As shown by FIGS. 6a and 6b, when a component piece of a medical device is composed of an oxygen-sensitive polymeric material, the device itself becomes an oxygen indicator, and any ambiguity about whether the device has been exposed to oxygen is removed.

The method for producing the storage arrangement of the present invention involves placing an oxygen-sensitive material 102, for example, Dow Calibre™ 2081 polycarbonate resin, inside a gas-impermeable sealable container 101. In some embodiments, a product 103, such as, for example, a medical product or food product, will also be placed into the sealable container 101. In one embodiment, the sealable container is a foil pouch 105. As discussed above, the oxygen-sensitive material 102 can be any material that visually indicates the presence of oxygen after exposure to radiation. As discussed above, the oxygen-sensitive material 102 can comprise a polycarbonate resin. Furthermore, the oxygen-sensitive material 102 may be formed into any desired shape or size depending upon the application.

Before being placed inside the sealable container, the oxygen-sensitive material 102 optionally can be attached to a background material 110 to enhance the visibility of the visual change. In addition, the oxygen-sensitive material 102, and the optional background material 110, can be either fixed inside the container or can be free-moving inside the container. By fixed inside the sealable container 101, it is meant that the oxygen-sensitive material 102 is directly attached to the inside of the sealable container 101. In embodiments where the oxygen-sensitive material is fixed inside the sealable container 101, any conventional method of attachment, including adhesives and mechanical fasteners, may be used that does not interfere with the function of the oxygen-sensitive material 102. Conversely, the term "free-moving" is intended to describe embodiments of the present invention where the oxygen-sensitive material 102 is not attached directly to the inside of the sealable container 101.

The atmospheric contents of the sealable container 101 are then removed by either vacuum or by purging the sealable container 101 with an inert gas such as nitrogen, carbon dioxide, argon or helium. In one embodiment, a vacuum is used to remove the atmospheric contents because a higher percent of oxygen, or atmospheric gas, can be removed in a shorter period of time as compared to purging. If the atmospheric contents of the container are removed by a vacuum, the sealable container 101 may be subsequently filled with an inert gas. In some embodiments, the ability of the oxygen-sensitive materials 102 to visually indicate the presence of oxygen is not dependent upon the choice of inert gas used as the controlled environment. Furthermore, the oxygen-sensitive materials 102 of the present invention can also function in applications where the controlled environment is a vacuum.

Once the atmospheric contents have been removed from the sealable container 101, the sealable container 101 will be substantially free of oxygen. As described above, the sealable container 101 can be filled with a substantially oxygen-free gas. The substantially oxygen-free gas can be nitrogen, helium, argon, carbon dioxide or some other inert gas. In some embodiments, the sealable container 101 is not filled with a substantially oxygen-free gas, and in those embodiments the controlled inert environment is a vacuum. The sealable container 101 is then sealed to isolate the oxygen-sensitive material 102 from the ambient atmosphere. As noted above, the sealable container 101 may be sealed by any conventional means known in the packaging industry including, but not limited to, thermal, adhesive or mechanical closures. In embodiments where the sealable container is a foil pouch 105, a heat press can be used to seal the foil pouch. The choice of sealing means will generally be determined by the particular choice of container being employed in a specific application.

The sealed container, including any contents or products contained within the sealed container, can then be irradiated with an effective amount of radiation to activate the oxygen-sensitive material 102. As discussed above, the sealable container can isolate foods, medical devices, pharmaceuticals, or other products from the ambient atmosphere. In some embodiments, the radiation used to activate the oxygen-sensitive material 102 is gamma radiation. In other embodiments of the present invention, the radiation used to activate the oxygen-sensitive material is X-ray radiation. In one embodiment, where the oxygen-sensitive material comprises Dow Calibre™ 2081, an effective amount of gamma radiation to activate the oxygen-sensitive material has been found to be from about 25 Kilograys to about 45 Kilograys.

Figure 7A:
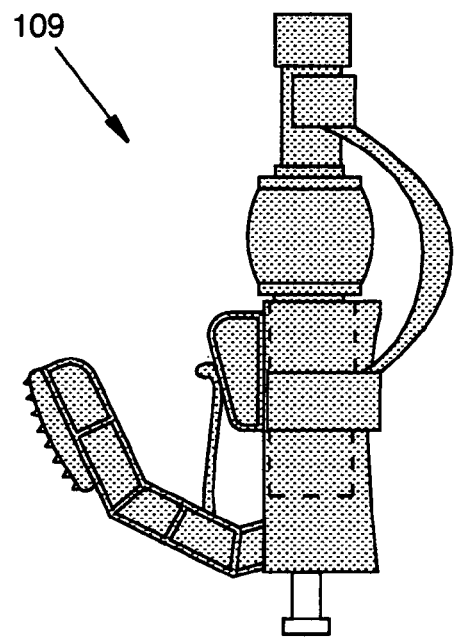
Figure 7B:
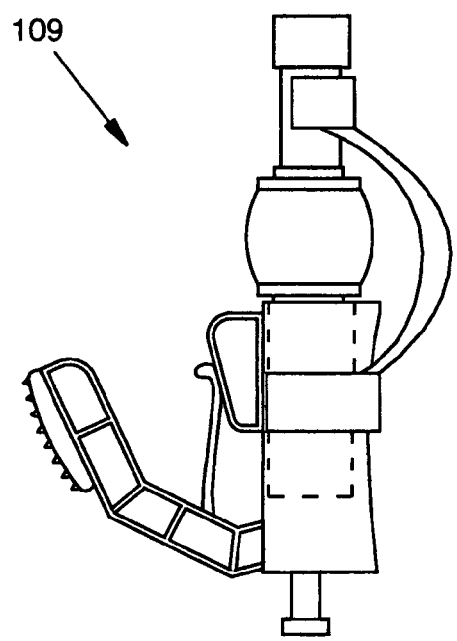

In the embodiment of the present invention where the oxygen-sensitive material 102 is Dow Calibre™ 2081, the gamma radiation can visually change the oxygen-sensitive material 102 from a purple color to a yellow-gray color. In this embodiment, once this color change has occurred, the oxygen-sensitive material 102 has been activated. Once activated, the Dow Calibre™ 2081 material will undergo a visual color change when exposed to oxygen. Prior to being activated, some of the oxygen-sensitive materials 102 of the present invention will not undergo a visual change when exposed to oxygen. As a result, some of the unactivated oxygen-sensitive materials of the present invention can be handled and stored in oxygen-rich environments. This feature of the oxygen-sensitive materials of the present invention facilitates easier storage and processing of the sensor materials as compared to other chemical oxygen indicators. FIGS. 7a and 7b show one example of a visual change associated with one embodiment of the present invention involving crimper devices 109 formed of oxygen-sensitive material where the oxygen-sensitive material comprises Dow Calibre™ 2081. The crimper device 109 shown in FIG. 7a has been exposed to oxygen for one week, while the crimper device 109 shown in FIG. 7b has just been removed from a substantially oxygen-free environment. The stippling in FIG. 7a represents a change in color from the showing in FIG. 7b.

The embodiments are intended to be illustrative and not limiting. Additional embodiments are within the claims. Although the present invention has been described with reference to particular embodiments, workers skilled in the art will recognize that changes may be made in form and detail without departing from the spirit and the scope of the invention.

What is claimed is:

1. A storage arrangement for an oxygen sensitive device including provision for indicating the presence of oxygen within the storage arrangement comprising:
   a. a sealable container that isolates contents of the sealable container from ambient atmosphere when sealed;
   b. an oxygen sensitive device located within the sealable container, the oxygen sensitive device having the form of a product or apparatus such that the oxygen sensitive device is configured for use in a procedure other than the sensing of oxygen, for example as a medical device useful in a medical procedure; and,
   c. an oxygen sensor having an oxygen-sensitive material of a polycarbonate mixture, the polycarbonate mixture designed for color stability when exposed to radiation, located within the sealable container separate from the oxygen device, the oxygen-sensitive material being inactive prior to exposure to radiation and activatible by exposure to radiation, the activation of the oxygen-sensitive material causing the oxygen-sensitive material to become sensitive to oxygen exposure only after activation and to remain sensitive to oxygen exposure after completion of radiation exposure and to undergo a visual change in response to subsequent contact with oxygen, the oxygen sensor having a configuration such that the only utility of the oxygen sensor is as a sensor, the oxygen sensor being located within the sealable container separate from the oxygen sensitive device such that the oxygen sensor is not part of said oxygen sensitive device nor any other device that may be included within said sealable container.

2. The storage arrangement of claim 1, wherein the oxygen sensor is fixed inside the sealable container.

3. The storage arrangement of claim 1, wherein the visual change of the oxygen sensor indicates a failure of the sealable container.

4. The storage arrangement of claim 1, wherein the radiation exposure is exposure to an effective amount of gamma radiation.

5. The storage arrangement of claim 4, wherein the effective amount of gamma radiation is from about 25 kilograys to about 45 kilograys.

6. The storage arrangement of claim 1, wherein the sealable container comprises:
   a. a gas impermeable foil pouch; and,
   b. a cardboard protective packaging for the foil pouch.

7. The storage arrangement of claim 6, wherein the gas impermeable foil pouch is a multi-layer package comprising:
   a. a silicone oxide treated PET layer;
   b. a foil layer;
   c. a biaxially oriented nylon layer; and,
   d. a polyethylene layer.

8. The storage arrangement of claim 1, wherein the oxygen-sensitive sensor is formed as a generally planar chip of the oxygen-sensitive material and is operably positioned adjacent to a backing material such that a combination of the backing material and the planar chip of the oxygen-sensitive material increases effective visibility of the visual change in the oxygen-sensitive material over visibility of visual change in the oxygen-sensitive material alone.

9. The storage arrangement of claim 1, wherein the oxygen-sensitive material undergoes the visual change within eight hours after exposure to a significant amount of oxygen after completion of radiation exposure.

10. The storage arrangement of claim 1, wherein the oxygen-sensitive material is arranged to form at least one symbol that assists in interpreting the visual change of the oxygen-sensitive material.

11. The storage arrangement of claim 10, wherein the at least one symbol includes at least one letter.

12. The storage arrangement of claim 1, wherein the visual change is a color change of the oxygen-sensitive material.

13. The storage arrangement of claim 1, wherein the oxygen sensitive device is a medical device.

14. The storage arrangement of claim 13, wherein the medical device is a distal occlusion inflation device.

15. The storage arrangement of claim 1, wherein the oxygen sensor is free-moving within the sealable container.

* * * * *